United States Patent [19]
Ikawa et al.

[11] Patent Number: 6,060,602
[45] Date of Patent: May 9, 2000

[54] COMPOUNDS FOR PRODUCING 2-NAPHTHAMIDE DERIVATIVE

[75] Inventors: Hiroshi Ikawa, Tokyo; Masato Nishimura, Oume, both of Japan

[73] Assignee: Fujirebio Inc., Tokyo, Japan

[21] Appl. No.: 09/216,852

[22] Filed: Dec. 21, 1998

Related U.S. Application Data

[62] Division of application No. 08/868,149, Jun. 3, 1997, Pat. No. 5,917,046, which is a division of application No. 08/657,545, Jun. 4, 1996, Pat. No. 5,714,613.

[30] Foreign Application Priority Data

| Jun. 5, 1995 | [JP] | Japan | 7-160161 |
| Jun. 5, 1995 | [JP] | Japan | 7-160162 |
| Jun. 5, 1995 | [JP] | Japan | 7-160163 |

[51] Int. Cl.[7] .............................. C07D 213/30
[52] U.S. Cl. ............................. 546/342
[58] Field of Search ............................. 546/342

[56] References Cited

U.S. PATENT DOCUMENTS

| 4,457,935 | 7/1984 | Iwao et al. | 548/201 |
| 5,324,728 | 6/1994 | Sekine et al. | 514/252 |

FOREIGN PATENT DOCUMENTS

0 492 178   7/1992   European Pat. Off. .

OTHER PUBLICATIONS

Tetrahedron, vol. 48, No. 43, pp. 9503–9516, 1992, The Oxidative Cross–Coupling of Substituted 2–Naphthols, Part I: The Scope and Limitations[1], Hovorka et al.

*Primary Examiner*—Jane Fan
*Attorney, Agent, or Firm*—Oblon, Spivak, McClelland, Maier & Neustadt, P.C.

[57] ABSTRACT

A method of producing a 2-naphthamide derivative of formula (I) that can be employed as an antiallergic agent or an agent for curing allergosis, and compounds for producing the 2-naphthamide derivative are provided:

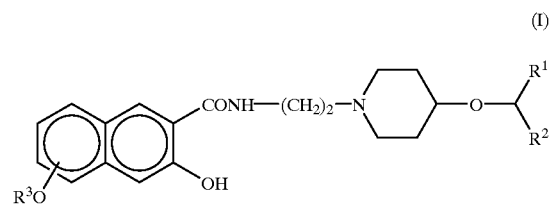

(I)

wherein $R^1$ and $R^2$ are each independently an unsubstituted or substituted aromatic hydrocarbon group, or an unsubstituted or substituted aromatic heterocyclic group; $R^3$ is an acyl group, an alkoxylcarbonyl group, a substituted carbamoyl group, or an unsubstituted or substituted alkyl group.

3 Claims, No Drawings

COMPOUNDS FOR PRODUCING 2-NAPHTHAMIDE DERIVATIVE

This application is a div. of Ser. No. 08/868,149 Jun. 3, 1997 now U.S. Pat. No. 5,917,046 which is a div. of Ser. No. 08/657,545 Jun. 4, 1996 U.S. Pat. No. 5,714,613.

BACKGROUND OF THE INVENTION

1. Field of the Invention

The present invention relates to a method of producing a 2-naphthamide derivative that can be employed as an anti-allergic agent or an agent for curing allergosis, and also to compounds for producing the 2-naphthamide derivative.

2. Discussion of Background

Conventionally, a 3-hydroxy-2-naphthamide derivative is produced, for example, by any of the following three methods, as disclosed in U.S. Pat. No. 5,324,728:

(1) the hydroxyl group at position 3 of the 3-hydroxy-2-naphthoic acid derivative is protected with an acyl group. The carboxyl group of the thus protected 3-hydroxy-2-naphthoic acid derivative is then chlorinated, for example, by thionyl chloride, to obtain a protected 3-hydroxy-2-naphthoic acid chloride derivative. The thus obtained protected 3-hydroxy-2-naphthoic acid chloride derivative is then allowed to react with an amine compound to obtain a protected 3-hydroxy-2-naphthamide derivative. However, according to this method, it is necessary to remove the acyl group employed for the above-mentioned protection of the hydroxyl group.

(2) A 3-hydroxy-2-naphthoic acid derivative is allowed to react with a carbodiimide reagent to produce a carbodiimide-reagent adduct. This adduct is then allowed to react with an amine compound.

(3) The first mentioned protected 3-hydroxy-2-naphthoic acid chloride derivative or the above-mentioned carbodiimide-reagent adduct is allowed to react with an alcohol compound such as a nitrophenol compound or N-hydroxysuccinimide compound to obtain an active ester compound. The thus obtained active ester compound is then allowed to react with an amine compound.

The first method (1), however, has the shortcomings that a step of protecting the hydroxyl group is required and that much by-products are produced since the reactions are carried out via unstable intermediates.

The second method (2) has the shortcomings that not only an expensive carbodiimide agent is required, but also, there must be conducted a difficult purification step for removing urea which is produced in a large amount in the reaction mixture.

The third method (3) has the shortcomings that complicated production stops are involved since after the protected 3-hydroxy-2-naphthoic acid chloride derivative or the carbodiimide-reagent adduct is produced, an alcohol compound has to be reacted therewith.

Thus, the above-mentioned 3-hydroxy-2-naphthamide derivative cannot be produced easily and with high yield by the conventional methods, and therefore such conventional methods are unsatisfactory as an industrially applicable method for producing the 3-hydroxy-2-naphthamide derivative.

SUMMARY OF THE INVENTION

It is therefore a first object of the present invention to provide a method of producing a 2-naphthamide derivative of formula (I),

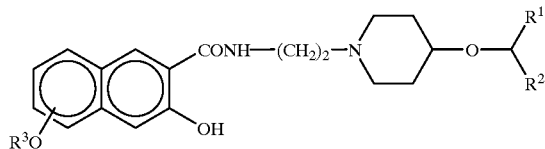

(I)

wherein $R^1$ and $R^2$ are each independently an unsubstituted or substituted aromatic hydrocarbon group, or an unsubstituted or substituted aromatic heterocyclic group; $R^3$ is an acyl group, an alkoxylcarbonyl group, a substituted carbamoyl group, or an unsubstituted or substituted alkyl group, easily and with high yield.

A second object of the present invention is to provide a compound for producing the above-mentioned 2-naphthamide derivative of formula (I).

A third object of the present invention is to provide another compound for producing the above-mentioned 2-naphthamide derivative of formula (I).

The first object of the present invention can be achieved by a method comprising the stop of allowing a 1,3-dioxan-4-one derivative of formula (II),

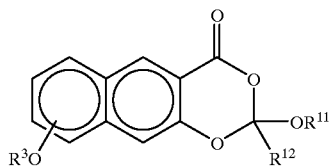

(II)

wherein $R^3$ is the same as defined in formula (I); $R^{11}$ is an unsubstituted or substituted alkyl group, an unsubstituted or substituted aromatic hydrocarbon group, or an unsubstituted or substituted aromatic heterocyclic group; and $R^{12}$ is an unsubstituted or substituted alkyl group, to react with an aminoethylpiperidine derivative of formula (III),

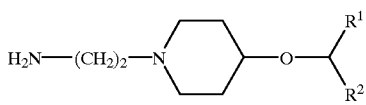

(III)

wherein $R^1$ and $R^2$ are respectively the same as defined in formula (I).

The first object of the present invention can also be achieved by a method comprising the step of:

allowing a compound of formula (VI),

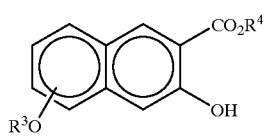

(VI)

wherein $R^1$ is the same as defined in formula (I), and
$R^4$ is an unsubstituted or substituted alkyl group having 1 to 6 carbon atoms, to react with an aminoethylpiperidine derivative of formula (III),

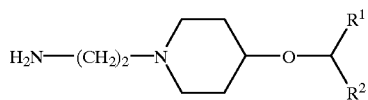
(III)

wherein $R^1$ and $R^2$ are respectively the same as defined in formula (I).

In the above reaction, the compound of formula (VI) can be prepared by allowing a dihydroxy-naphthoic acid ester derivative of formula (IV),

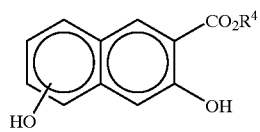
(IV)

wherein $R^4$ is the same as defined in formula (VI), to react with an alcohol derivative of formula (V), $R^3$—OH (V)

wherein $R^3$ is the same an defined in formula (I).

Alternatively, the first object of the present invention can be achieved by a method comprising the step of:

allowing an acid anhydride derivative of formula (VII),

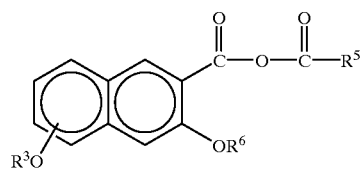
(VII)

wherein $R^3$ is the same as defined in formula (I), and $R^5$ an unsubstituted or substituted alkyl group having 1 to 5 carbon atoms; $R^6$ is a hydrogen atom, or

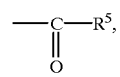

to react with an aminoethylpiperidine derivative of formula (III),

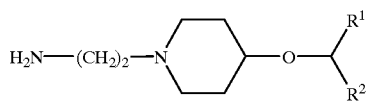
(III)

wherein $R^1$ and $R^2$ are respectively the same as defined in formula (I), to produce a reaction product corresponding to said 2-naphthamide derivative of formula (I), with the hydrolysis of the reaction product only when $R^6$ is

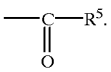

In the above method, the acid anhydride derivative of formula (VII) can be prepared by the step of:

allowing a naphthoic acid derivative of formula (VIII),

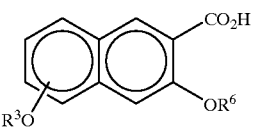
(VIII)

wherein $R^4$ is the same as defined in formula (I), to react with an acyl derivative of formula (IX), $R^5COX^1$ (IX)

wherein $R^5$ is the same as defined in formula (VII), and $X^1$ is a halogen atom.

The second object of the present invention can be achieved by a 1,3-dioxan-4-one derivative of formula (II-a),

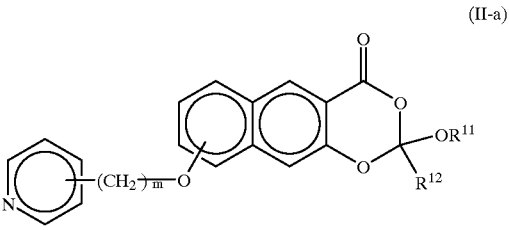
(II-a)

wherein $R^{11}$ is an unsubstituted or substituted alkyl group, an unsubstituted or substituted aromatic hydrocarbon group, or an unsubstituted or unsubstituted aromatic heterocyclic group; $R^{12}$ is an unsubstituted or substituted alkyl group; and m is an integer of 1 to 6.

The third object of the present invention can be achieved by a compound of formula (VI-a),

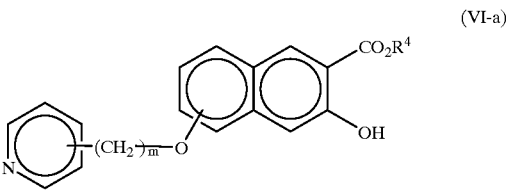
(VI-a)

wherein $R^4$ is an unsubstituted or substituted alkyl group having 1 to 6 carbon atoms.

DESCRIPTION OF THE PREFERRED EMBODIMENTS

According to the present Invention, there is provided a method of producing a 2-naphthamide derivative of formula (I) in accordance with the following reaction scheme I:

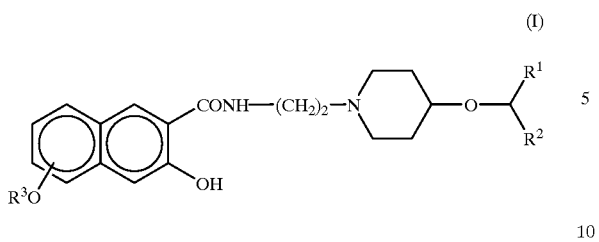

(I)

wherein $R^1$ and $R^2$ are each independently an unsubstituted or substituted aromatic hydrocarbon group, or an unsubstituted or substituted aromatic heterocyclic group; $R^3$ is an acyl group, an alkoxylcarbonyl group, a substituted carbamoyl group, or an unsubstituted or substituted alkyl group.

Reaction Scheme I

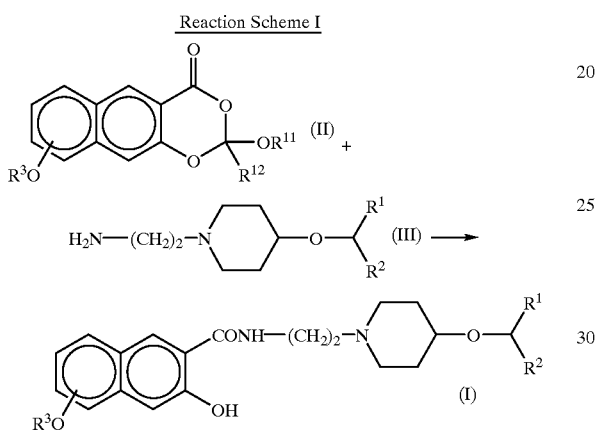

The above method comprises the step of: allowing a 1,3-dioxan-4-one derivative of formula (II),

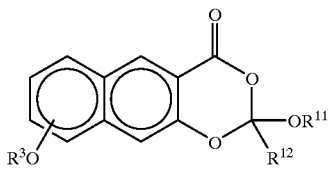

(II)

wherein $R^3$ is the same as defined in formula (I); $R^{11}$ is an unsubstituted or substituted alkyl group, an unsubstituted or substituted aromatic hydrocarbon group, or an unsubstituted or substituted aromatic heterocyclic group; and $R^{12}$ is an unsubstituted or substituted alkyl group, to react with an aminoethylpiperidine derivative of formula (III),

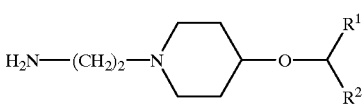

(III)

wherein $R^1$ and $R^2$ are respectively the same as defined in formula (I).

The above 1,3-dioxan-4-one derivative of formula (II) can be produced in accordance with the following Reaction Scheme I-a:

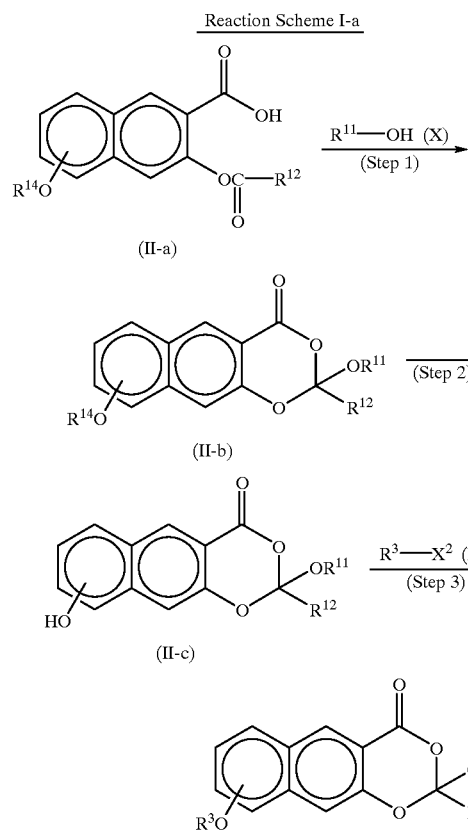

wherein $R^{11}$, $R^{12}$ and $R^3$ are respectively the same as defined previously; $R^{14}$ may be the same as $R^3$; and $X^2$ is a hydroxyl group or a halogen atom such as bromine, chlorine or iodine.

[Step 1]

In this step, the 2-naphthoic acid derivative of formula (II-a) is allowed to react with an alcohol derivative of formula (X) in the presence of an acid anhydride for cyclization reaction, whereby a 1,3-dioxan-4-one derivative of formula (II-b) is produced.

In the 2-naphthoic acid derivative of formula (II-a), $R^{12}$ is an unsubstituted or substituted alkyl group.

Examples of such an alkyl group are a straight-chain, branched or cyclic alkyl group having 1 to 6 carbon atoms, such as methyl group, ethyl group, propyl group, butyl group, pentyl group, hexyl group, isopropyl group, 2-butyl group, t-butyl group, cyclopentyl group and cyclohexyl group.

Examples of a substituent of these alkyl groups are an unsubstituted or substituted phenyl group; an alkoxyl group having 1 to 6 carbon atoms, such as methoxy group, ethoxy group, propoxy group, butoxy group, pentyloxy group, and hexyloxy group; cyano group; nitro group; and a halogen atom such as chlorine, bromine and iodine.

$R^{14}$ may be an acyl group, an alkoxycarbonyl group, or a substituted carbamoyl group.

Specific examples of the acyl group are acetyl group, propionyl group, isopropionyl group, butyryl group, isobutyryl group, varelyl group, benzoyl group, toluoyl group, and naphthoyl group.

Specific examples of the alkoxylcarbonyl group are mothoxycarbonyl group, ethoxycarbonyl group, propoxycarbonyl group, butoxycarbonyl group, phenoxycarbonyl group, and banzyloxycarbonyl group.

Specific examples of the substituted carbamoyl group are methylcarbamoyl group, ethylcarbamoyl group, propylcarbamoyl group, butylcarbamoyl group, phenylcarbamoyl group, benzylcarbamoyl group, naphthylcarbamoyl group, dimethylcarbamoyl group, and diethylcarbamoyl group.

A 2-naphthoic acid derivative of formula (II-a) can be produced, for example, in accordance with a procedure described in Japanese Laid-Open Patent Application 4-364156, from a 2-naphthoic acid derivative having a hydroxyl group as a substituent.

Specific examples of the 2-naphthoic acid derivative of formula (II-a) are 3,5-diacetoxy-2-naphthoic acid, 3-acetoxy-5-(3-pyridylmethoxy)-2-naphthoic acid, 3-acetoxy-5-(2-pyridylmethoxy)-2-naphthoic acid, 3,7-diacetoxy-2-naphthoic acid, 3,4-diacetoxy-2-naphthoic acid, 3,6-diacetoxy-2-naphthoic acid, 3,8-diacetoxy-2-naphthoic acid, 3-acetoxy-5-benzyloxy-2-naphthoic acid, and 3-acetoxy-5-methoxy-2-naphthoic acid.

The alcohol compound of formula (X) is an alcohol compound with the moiety $R^{11}$ thereof being an unsubstituted or substituted alkyl group, an unsubstituted or substituted aromatic hydrocarbon group, or an unsubstituted or substituted aromatic heterocyclic group.

Examples of the alkyl group represented by $R^{11}$ may be the same as those represented by $R^{12}$.

Examples of the aromatic hydrocarbon group represented by $R^{11}$ are phenyl group and naphthyl group; and examples of the aromatic heterocyclic group represented by $R^{11}$ are furyl group, thienyl group and pyridyl group.

Such alcohol compounds are industrially easily available. Specific examples of the alcohol compound of formula (X) are methanol, ethanol, propanol, butanol, pentanol, hexanol, phenol, 1-naphthol and 2-naphthol.

The reaction between the 2-naphthoic acid derivative of formula (II-a) and the alcohol compound of formula (X) is carried out in the presence of an acid anhydride.

Examples of the acid anhydride for use in this reaction are trifluoroacetic anhydride, acetic anhydride, trichloroacetic anhydride, propionic anhydride, phenylacetic anhydride, methanesulfonic anhydride, and p-toluenesulfonic anhydride.

It is preferable that the above acid anhydride be employed in an amount of 1 to 2 equivalents for one mole of the 2-naphthoic acid derivative of formula (II-a).

It is also preferable that the above reaction be carried out in an inert solvent.

Examples of the inert solvent for use in this reaction are nitriles such as acetonitrile and propionitrile; ethers such as diethyl ether, dimethoxyethane (DME), tetrahydrofuran and dioxane; aromatic hydrocarbons such as benzene, toluene and xylene; esters such as ethyl acetate; and amides such as dimethylformamide (DMF). These solvents can be used alone or in combination.

The reaction can usually be carried out at temperatures in the range of −78° C. to 200° C., but in view of the efficiency of the reaction, it is preferable that the reaction be carried out at temperatures in the range of 0° C. to 100° C.

Furthermore, it is preferable that this reaction be carried out under the conditions free from water, in an atmosphere of an inert gas, such as nitrogen or argon, in order to obtain the desired product in high yield.

[Step 2]

In this step, the 1,3-dioxan-4-one derivative of formula (II-b) produced in Step 1 is deprotected, whereby a 1,3-dioxan-4-one derivative of formula (II-c) is produced.

It is preferable that the above deprotection be carried out in the presence of a base. Examples of the base for use in the deprotection reaction are organic bases such as piperidine, ammonia, methylamine, ethylamine, propylamine, butylamine, triethylamine, pyridine and pyrrolidine; and inorganic bases such as hydrazine, potassium carbonate, sodium carbonate, sodium hydroxide, and potassium hydroxide.

The above bases may be employed in an amount of 1 to 2 equivalents for one mole of the 2-naphthoic acid derivative of formula (II-b).

It is preferable that the above reaction be carried out in an inert solvent.

Examples of the inert solvent for use in this reaction are nitriles such as acetonitrile and propionitrile; ethers such as diethyl ether, dimethoxyethane (DME), tetrahydrofuran and dioxane; aromatic hydrocarbons such as benzene, toluene and xylene; esters such as ethyl acetate; and amides such as dimethylformamide (DMF). These solvents can be used alone or in combination.

The reaction can usually be carried out at temperatures in the range of −78° C. to 200° C., but in view of the efficiency of the reaction, it is preferable that the reaction be carried out at temperatures in the range of 0° C. to 80° C.

[Step 3]

In this step, the 1,3-dioxan-4-one derivative of formula (II-c) produced in Step 2 and the compound of formula (XI) are subjected to a condensation reaction, whereby the 1,3-dioxan-4-one derivative of formula (II) is produced.

In the compound of formula (XI), $R^3$ is an acyl group, an alkoxycarbonyl group, a substituted carbamoyl group, or an unsubstituted or substituted alkyl group.

The alkyl group represented by $R^3$ may be a straight-chain, branched or cyclic alkyl group having 1 to 6 carbon atoms, such as methyl group, ethyl group, propyl group, butyl group, pentyl group, hexyl group, isopropyl group, 2-butyl group, t-butyl group, cyclopentyl group, and cyclohexyl group.

Examples of a substituent of the above alkyl group are aromatic hydrocarbon group such as phenyl group and naphthyl group; and aromatic heterocyclic group such an furyl group, thienyl group and pyridyl group.

Specific examples of the halogen atom represented by $X^2$ are chlorine, bromine and iodine.

When the reaction in Step 3 is carried out by use of the compound of formula (XI) in which $X^2$ in a halogen atom, it is preferable that the reaction be carried out in the presence of a base. Examples of the base for use in the above reaction are organic bases such as triethylamine, pyridine, piperidine, and dimethylaminopyridine; and inorganic bases such as hydrazine, sodium carbonate, sodium hydrogencarbonate, potassium carbonate, sodium hydroxide, and potassium hydroxide.

It is also preferable that the above reaction be carried out in the absence of solvent, or in an inert solvent.

When an inert solvent is used in this reaction, examples of the inert solvent are nitriles such as acetonitrile and propionitrile; and ethers such as diethyl ether, dimethoxyethane (DME), tetrahydrofuran and dioxane. These solvents can be used alone or in combination.

The reaction can usually be carried out at temperatures in the range of −78° C. to 200° C., but in view of the efficiency of the reaction, it is preferable that the reaction be carried out at temperatures in the range of 0° C. to 200° C.

When the reaction in Step 3 is carried out by use of the compound of formula (XI) in which $X^2$ is a hydroxyl group, it is preferable that the reaction be carried out in the presence of a condensation agent such as Mitsunobu agent.

The above reaction can be carried out at the temperatures in the same range and also in the same solvents as in the case where the reaction is carried out by use of the compound of formula (XI) in which $X^2$ is a halogen atom.

The thus produced 1,3-dioxan-4-one derivative of formula (II) is allowed to react with an aminoethylpiperidine derivative of formula (III),

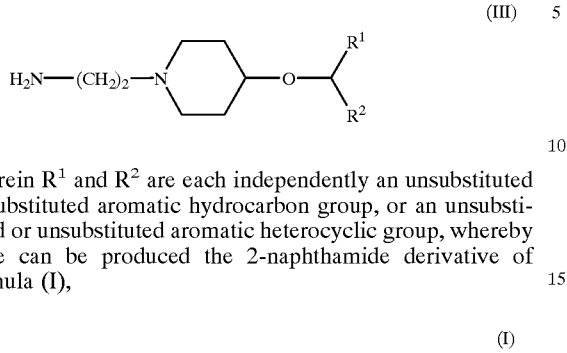

wherein $R^1$ and $R^2$ are each independently an unsubstituted or substituted aromatic hydrocarbon group, or an unsubstituted or unsubstituted aromatic heterocyclic group, whereby there can be produced the 2-naphthamide derivative of formula (I),

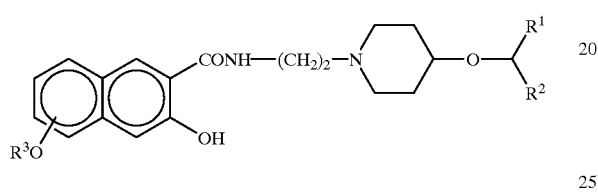

wherein $R^1$ and $R^2$ are each independently an unsubstituted or substituted aromatic hydrocarbon group, or an unsubstituted or unsubstituted aromatic heterocyclic group; $R^3$ is an acyl group, an alkoxylcarbonyl group, a substituted carbamoyl group, or an unsubstituted or substituted alkyl group.

According to the present invention, the 2-naphthamide derivative of formula (I) can also be produced in accordance with the following reaction scheme II:

Reaction Scheme II

[Step 1]

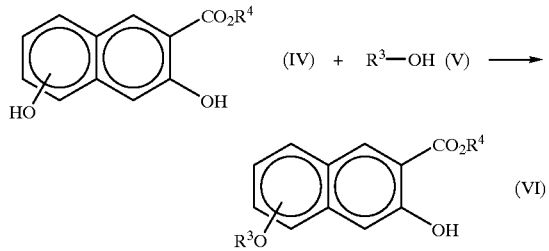

[Step 2]

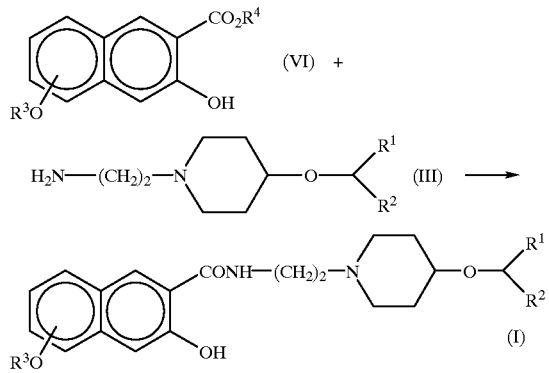

More specifically, the above method comprises the steps of:
allowing a dihydroxynaphthoic acid ester derivative of formula (IV),

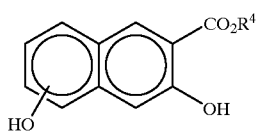

wherein $R^4$ is an unsubstituted or substituted alkyl group having 1 to 6 carbon atoms, to react with an alcohol derivative of formula (V),

wherein $R^3$ is the same as defined in formula (I), to obtain a compound of formula (VI),

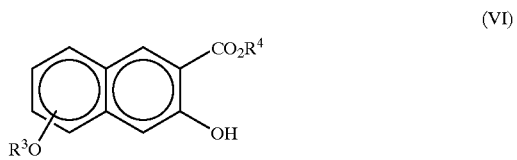

wherein $R^3$ is the same as defined in formula (I), and $R^4$ is the same as defined in formula (IV), and
allowing the compound of formula (VI) to react with an aminoethylpiparidine derivative of formula (III),

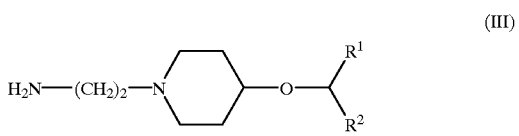

wherein $R^1$ and $R^2$ are respectively the same as defined in formula (I).

For example, in the above reaction, when the dihydroxynaphthoic acid enter derivative of formula (IV) is the following dihydronaphthoic acid ester derivative of formula (IV-a),

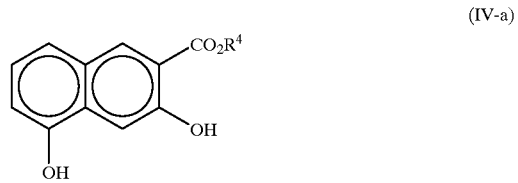

wherein $R^4$ is an unsubstituted or substituted alkyl group having 1 to 6 carbon atoms, and the alcohol derivative of formula (V) is an alcohol derivative of formula (V-a),

wherein m is an integer of 1 to 6, the above reaction can be carried out in the presence of a phosphorus compound and an azo compound, whereby there can be obtained a compound of formula (VI-b),

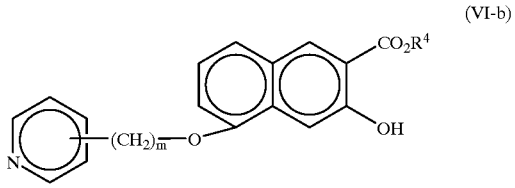

(VI-b)

wherein $R^4$ and m are respectively the same as defined previously.

In the previously mentioned formulae (VI), (VI-a) and (VI-b), specific examples of the alkyl group represented by $R^4$ are methyl group, ethyl group, propyl group, isopropyl group, n-butyl group, sec-butyl group, t-butyl group, pentyl group and hexyl group.

The alkyl group represented by $R^4$ may have a substituent.

Examples of a substituent of the above alkyl group represented by $R^4$ are aromatic hydrocarbon group such as phenyl group and naphthyl group; and aromatic heterocyclic group such as furyl group, thienyl group and pyridyl group.

The dihydronaphthoic acid ester derivative of formula (IV-a) is easily available by esterification of a conventionally known corresponding 3,5-dihydroxynaphthoic acid.

Specific examples of the dihydronaphthoic acid ester derivative of formula (IV-a) are methyl 3,5-dihydroxy-2-naphthoate, ethyl 3,5-dihydroxy-2-naphthoate, propyl 3,5-dihydroxy-2-naphthoate, isopropyl 3,5-dihydroxy-2-naphthoate, n-butyl 3,5-dihydroxy-2-naphthoate, isobutyl 3,5-dihydroxy-2-naphthoate, t-butyl 3,5-dihydroxy-2-naphthoate, pentyl 3,5-dihydroxy-2-naphthoate, hexyl 3,5-dihydroxy-2-naphthoate, benzyl 3,5-dihydroxy-2-naphthoate, 2-pyridylmethyl 3,5-dihydroxy-2-naphthoate, and 2-pyridylmethyl 3,5-dihydroxy-3-naphthoate.

The alcohol derivative of formula (V-a) is easily available and specific examples thereof are 2-pyridinemethanol, 3-pyridinemethanol, 4-pyridinemethanol, 2-(2-hydroxyethyl)pyridine, 3-(2-hydroxyethyl)pyridine, 4-(2-hydroxyethyl)pyridine, 2-(1-hydroxyethyl)pyridine, 3-(3-hydroxypropyl)pyridines 3-(4-hydroxypropyl)pyridine, 3-(5-hydroxypropyl)pyridine, and 3-(6-hydroxypropyl)-pyridine.

As mentioned previously, the reaction for obtaining the compound of formula (VI-a) is carried out in the presence of a phosphorus compound and an azo compound.

The phosphorus compound is a compound represented by a formula of $P(R^{13})_3$ wherein $R^{13}$ is an alkyl group having 1 to 6 carbon atoms, phenyl group, dimethylamino group, diethylamino group, or dipropylamino group.

Specific examples of the alkyl group represented by $R^{13}$ may be the same as the examples of the alkyl group represented by $R^4$ in the previously mentioned formula (IV) or (IV-a).

Specific examples of the phosphorus compound represented by formula of $P(R^{13})_3$ are trimethylphosphine, triethylphosphine, tripropylphosphine, tributylphophine, hexamethylphosphorus triamide, and hexaethylphosphorus triamide.

Examples of the azo compound are alkylazocarboxylate compounds and azodicarboxyamide compounds. Specific examples of the above azo compounds are diethylazodicarboxylate, diisopropyl-azodicarboxylate, N,N,N',N'-tetramethylazodicarboxyamide, N,N,N',N'-tetraisopropylazodicarboxyamide, and 1,1'-(azodicarbonyl) dipiperidine.

It is preferable that the above reaction be carried out in an inert solvent.

Examples of the inert solvent for use in this reactsion are ethers such as diethyl ether, dimethoxyethane (DME), tatrahydrofuran, 1,4-dioxane and diglyme; aromatic hydrocarbons such as benzene, toluene and xylene; esters such as ethyl acetate; amides such as dimethylformamide (DMF); and nitriles such as acetonitrile and propionitrile. These solvents can be used alone or in combination.

The reaction can usually be carried out at temperatures in the range of −78° C. to 200° C., but in view of the efficiency of the reaction, it is preferable that the reaction be carried out at temperatures in the range of 0° C. to 100° C.

The compound of formula (VI-a) can also be prepared by allowing the previously mentioned 3,5-dihydroxynaphthoic acid ester derivative of formula (IV-a) to react with a pyridine compound of formula (V-b) in accordance with a procedure as described in U.S. Pat. No. 5,324,728.

(V-b)

The thus obtained compound of formula (VI-a), for example, a compound of formula (VI-b), can be allowed to react with an aminoethyl-piperidine derivative of formula (III), for example, 1-(2-aminoethyl)-4-benzhydryloxypiperidine which can be prepared by a method as described in U.S. Pat. No. 5,324,728, whereby there can be obtained a 2-naphthamide derivative of the following formula (I-b) in accordance with the following reaction scheme:

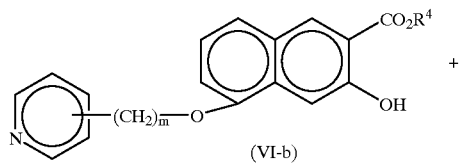

(VI-b)

+

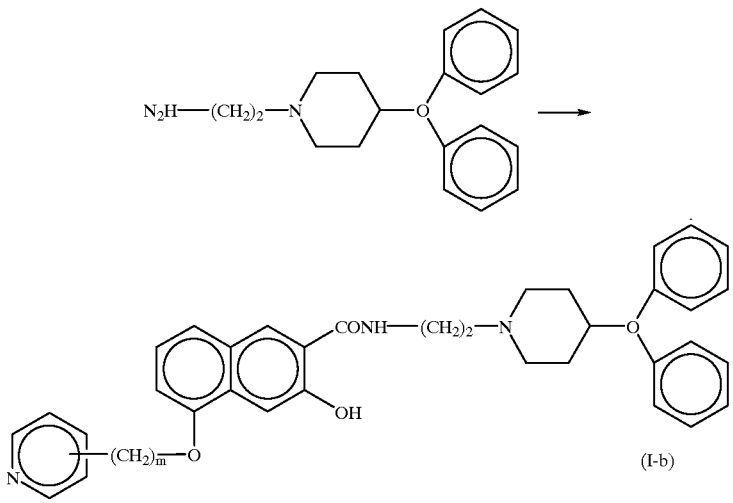

(I-b)

wherein m is the same as defined previously.

It is preferable that the above reaction be carried out in an inert solvent.

Examples of the inert solvent for use in this reaction are aromatic hydrocarbons such as benzene, toluene and xylene; ethers such as diethyl ether, dimethoxyethane (DME), tetrahydrofuran, 1,4-dioxane and diglyme; esters such as ethyl acetate; amides such as dimethylformamide (DMF); nitriles such as acetonitrile and propionitrile; and ketones such as acetone, and methyl ethyl ketone. These solvents can be used alone or in combination.

The reaction can usually be carried out at temperatures in the range of 0° C. to 300° C., but in view of the efficiency of the reaction, it is preferable that the reaction be carried out at temperatures in the range of 50° C. to 150° C.

Furthermore, in order to carry out this reaction more efficiently, it is preferable that the reaction be carried out in the presence of a base such as sodium hydride, n-butyl lithium, lithium diisopropyl amide (LDA) and t-butoxy potassium.

When such a base is added to the reaction solution, it is preferable that the amount of such a base be in the range of 0.1 to 2 moles for one mole of the compound of formula (VI-a).

Furthermore, according to the present invention, the 2-naphthamide derivative of formula (I) can also be produced in accordance with the following reaction scheme III:

Reaction Scheme III

[Step 1]

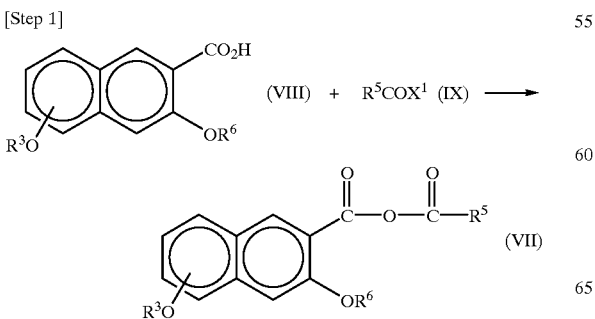

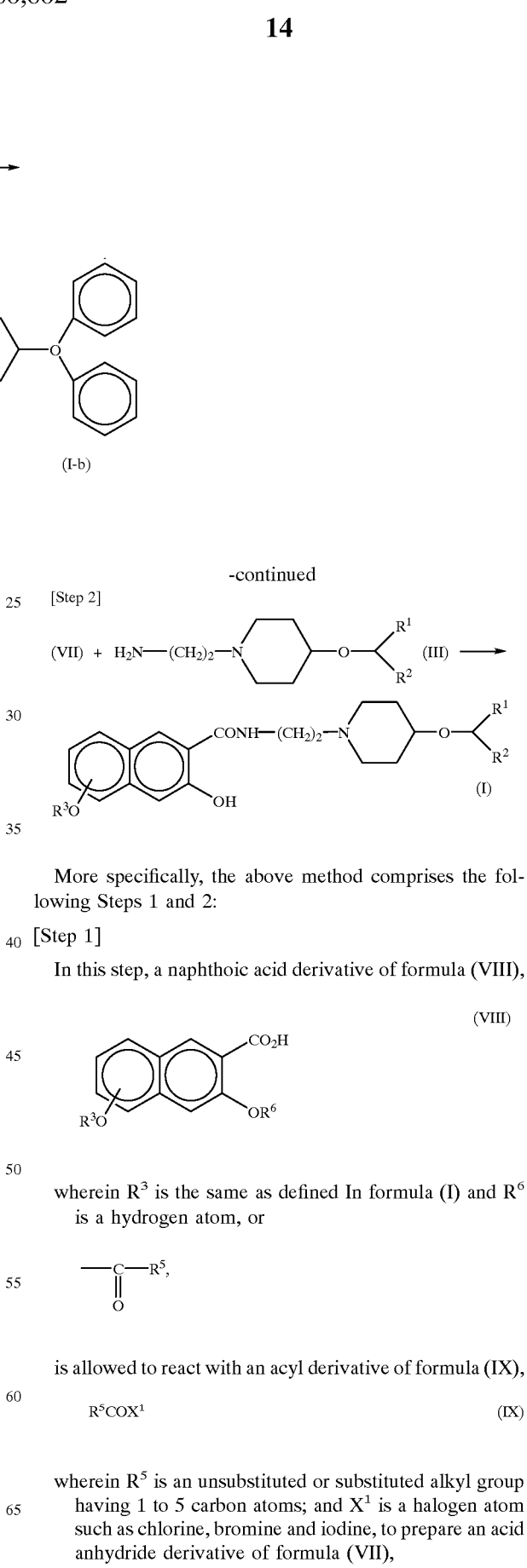

More specifically, the above method comprises the following Steps 1 and 2:

[Step 1]

In this step, a naphthoic acid derivative of formula (VIII), wherein $R^3$ is the same as defined In formula (I) and $R^6$ is a hydrogen atom, or $$-\underset{\underset{O}{\|}}{C}-R^5,$$

is allowed to react with an acyl derivative of formula (IX), $$R^5COX^1 \qquad (IX)$$

wherein $R^5$ is an unsubstituted or substituted alkyl group having 1 to 5 carbon atoms; and $X^1$ is a halogen atom such as chlorine, bromine and iodine, to prepare an acid anhydride derivative of formula (VII),

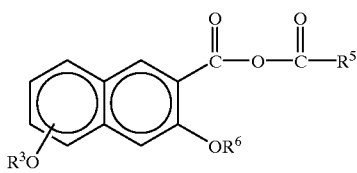
(VII)

wherein $R^3$ is the same as defined in formula (I), and $R^5$ and $R^6$ are respectively the same as defined in formula (VIII).

The acyl derivative of formula (IX) may be used in an amount of at least one mole for one of the naphthoic acid derivative of formula (VIII). However, in view of the reaction efficiency, it is preferable that the acyl derivative of formula (IX) be used in an amount of 1.1 to 1.3 moles for one of the naphthoic acid derivative of formula (VIII).

Specific examples of the above acyl derivative of formula (IX) are acetyl chloride, propionyl chloride, butyryl chloride, isobutyryl chloride, valeryl chloride, and pivaloyl chloride.

Examples of a substituent of the alkyl group represented by $R^5$ are phenyl group, naphthyl group and pyridyl group.

It is preferable that the above reaction be carried out in an inert solvent, preferably in the presence of a base for increasing the reaction efficiency.

Examples of the inert solvent for use in the above reaction are halogenated hydrocarbons such as methylene chloride, chloroform and dichloroethane; ethers such an diethyl ether, dimethoxy-ethane (DME), tetrahydrofuran, 1,4-dioxane and diglyme; aromatic hydrocarbons such as benzene, toluene and xylene; esters such as ethyl acetate; amides such as dimethyiformamide (DMF); and nitriles such as acetonitrile and propionitrile. These solvents can be used alone or in combination.

Examples of the base for use in the above reaction are organic bases such as triethylamine, diethylamine, pyridine, and collidine; and inorganic bases such as sodium hydroxide, potassium hydroxide, sodium carbonate, potassium carbonate, sodium hydrogencarbonate, and potassium hydrogencarbonate.

the above reaction can usually be carried out at temperatures in the range of –78° C. to 200° C., but in view of the efficiency of the reaction, it is preferable that the reaction be carried out at temperatures in the range of –10° C. to 80° C.

The formation of the acid anhydride derivative of formula (VII) in the above reaction can be easily confirmed or identified by a conventional analysis such as thin layer chromatography (TLC).

[Step 2]

In this step, the acid anhydride derivative of formula (VII) prepared in the above Step 1, without being isolated, is allowed to react with an aminoethylpiperidine derivative of formula (III),

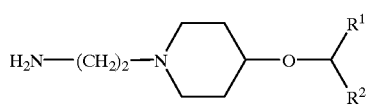
(III)

wherein $R^1$ and $R^2$ are respectively the same as defined in formula (I), to produce a reaction product corresponding to the 2-naphthamide derivative of formula (I).

It is preferable that the above reaction be carried out in an inert solvent in the presence of a base.

Examples of the inert solvent for use in the above reaction are halogenated hydrocarbons such as methylene chloride, chloroform and dichloroethane; ethers such as diethyl ether, dimethoxy-ethane (DME), tetrahydrofuran, 1,4-dioxane and diglyme; aromatic hydrocarbons such as benzene, toluene and xylene; esters such ad ethyl acetate; amides such as dimethylformamide (DMF); and nitriles such as acetonitrile and propionitrile. These solvents can be used alone or in combination.

Examples of the base for use in the above reaction are organic bases such as triethylamine, diethylamine, pyridine, and collidine; and inorganic bases such as sodium hydroxide, potassium hydroxide, sodium carbonate, potassium carbonate, sodium hydrogencarbonate, and potassium hydrogencarbonate.

It is preferable that the amount of such a base be at least one mole for one mole of the acid anhydride derivative of formula (VII).

The above reaction can usually be carried out at temperatures in the range of –78° C. to 200° C., but in view of the efficiency of the reaction, it is preferable that the reaction be carried out at temperatures in the range of –10° C. to 80° C.

When $R^6$ in formula (VII) is

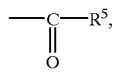

the previously mentioned reaction product corresponding to the 2-naphthamide derivative of formula (I) can be hydrolyzed by a conventional method in the presence of a base such as ammonia, hydrazine, sodium carbonate, potassium carbonate, sodium hydrogencarbonate, potassium hydrogen carbonate, sodium hydroxide, or potassium hydroxide.

It is preferable that this hydrolysis be performed in water or in a mixed solvent composed of a water-miscible organic solvent and water at temperatures in the range of –20° C. to 100° C.

Other features of this invention will become apparent in the course of the following description of exemplary embodiments, which are given for illustration of the invention and are not intended to be limiting thereof.

EXAMPLE 1

[Preparation of 9-acetoxy-2-methyl-2-benzyloxy-naphtho[2,3-e]-1,3-dioxan-4-one]

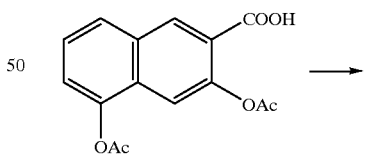

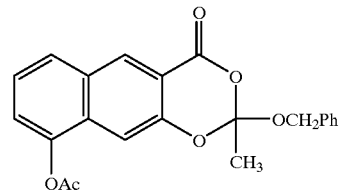

In a stream of nitrogen, 0.54 ml (3.82 mmol) of trifluoroacetic anhydride was added to a solution of 1 g (3.47 mmol) of 3,5-diacetoxy-2-naphthoic acid in 30 ml of tetrahydrofuran at room temperature. The mixture was stirred at 50° C. for 30 minutes.

To this mixture, 376 mg (3.47 mmol) of benzyl alcohol was added at room temperature. This reaction mixture was then stirred at 50° C. for 5 hours.

After the completion of the reaction, the solvent was distilled away from the reaction mixture, and the residue was extracted with ethyl acetate three times.

All the ethyl acetate extract layers were mixed and washed with a saturated aqueous solution of sodium chloride and dried over anhydrous magnesium sulfate. The solvent was distilled away from the mixture.

The residue was chromatographed on silica gel, whereby 9-acetoxy-2-methyl-2-benzyloxy-naphthol[2,3-e]-1,3-dioxan-4-one was obtained in a yield of 223 mg (18%).

IR(cm$^{-1}$, KBr) : 1758

NMR (δ, CDCl$_3$) : 1.95 (3H, s), 2.47 (3H, s), 4.82 (2H, dd, J=11 Hz, 11 Hz), 7.18–7.30 (5H, m), 7.37–7.50 (3H, m), 7,83 (1H, d, J=7 Hz), 8.65 (1H, s)

Mass (EI) : m/z 378(M'), 271,228,186

Melting Point: 155° C.–156° C.

EXAMPLE 2

[Preparation of 9-acetoxy-2-methyl-2-phenoxy-naphthol[2,3-e]-1, 3-dioxane-4-one]

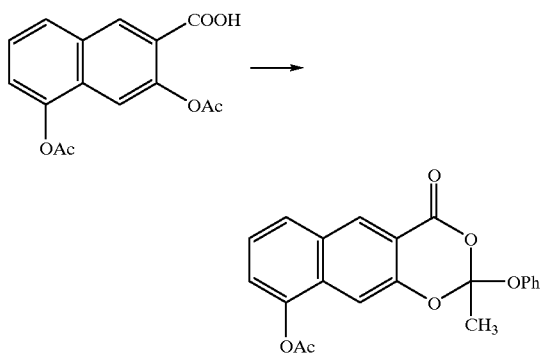

In a stream of nitrogen, 0.54 ml (3.82 mmol) of trifluoroacetic anhydride was added to a solution of 1 g (3.47 mmol) of 3,5-diacetoxy-2-naphthoic acid in 30 ml of tetrahydrofuran at room temperature. The mixture was stirred at 50° C. for 30 minutes.

To this mixture, 360 mg (3.82 mmol) of phenol was added at room temperature. This reaction mixture was then stirred at 50° C. for 5 hours.

After the completion of the reaction, the solvent was then distilled away from the reaction mixture, and the residue was extracted with ethyl acetate three times.

All the ethyl acetate extract layers were mixed and washed with a saturated aqueous solution of sodium chloride and dried over anhydrous magnesium sulfate. The solvent was distilled away from the mixture.

The residue was chromatographed on silica gel, whereby 9-acetoxy-2-methyl-2-phenoxy-naphthol[2,3-e]-1,3-dioxan-4-one was obtained in a yield of 1.0 g (79%).

IR(cm$^{-1}$, KBr) : 1756

NMR (δ, CDCl$_3$) : 1.95 (3H, s), 2.49 (3H, s), 7.09–7.18 (3H, m), 7.40(1H, dd, J=7 Hz, 7 Hz), 7.47(1H, dd, J=7 Hz, 7 Hz), 7.51 (1H, s), 7.85(1H, d, J=7 Hz), 8.70 (1H, s)

Mass (EI) : m/z 364(M'), 271,229,228,187

Melting Point: 156° C.–157° C.

EXAMPLE 3

[Preparation of 9-Hydroxy-2-methyl-2-phenoxy-naphthol[2,3-e]-1, 3-dioxane-4-one]

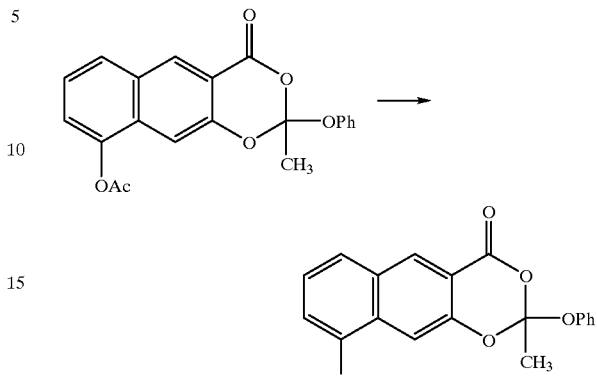

0.03 ml (0.3 mmol) of piperidine was added to a solution of 100 mg (0.27 mmol) of 9-acetoxy-2-methyl-2-phenoxy-naphthol[2,3-e]-1,3-dioxan-4-one prepared in Example 2 in 10 ml of acetonitrile at room temperature. The mixture was stirred for 15 hours.

After the completion of the reaction, the solvent was then distilled away from the reaction mixture, and the residue was extracted with ethyl acetate three times.

All the ethyl acetate extract layers were mixed and washed with a saturated aqueous solution of sodium chloride and dried over anhydrous magnesium sulfate. The solvent was distilled away from the mixture.

The residue was chromatographed on silica gel, whereby 9-hydroxy-2-methyl-2-phenoxy-naphthol[2,3-e]-1,3-dioxan-4-one was obtained in a yield of 78 mg (98%).

IR(cm$^{-1}$, KBr): 3296, 1726

NMR (δ, CDCl$_3$) : 1.95 (3H, s), 5.36 (1H, s), 6.93(1H, d, J=7 Hz), 7.10–7.18(3H, m), 7.25–7.35(2H, m), 7.54(1H, d, J=7 Hz), 7,86(1H, s), 8.63 (1H, s)

Mass (EI) ; m/z 322(M'), 280, 229,186

[Preparation of 2-Methyl-2-phenoxy-9-(3-pyridylmethoxy)-naphthol [2,3-e]-1,3-dioxane-4-one]

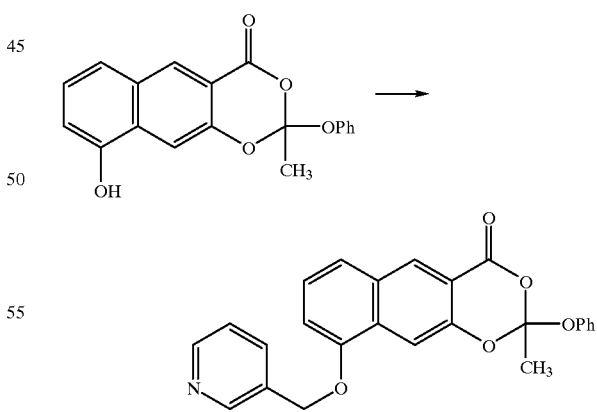

To a solution of 483 mg (1.5 mmol) of the above prepared 9-hydroxy-2-methyl-2-phenoxy-naphthol[2,3-e]-1,3-dioxan-4-one in 20 ml of tetrahydrofuran, 446 mg (1.7 mmol) of triphenylphosphine, 180 mg (1.65 mmol) of pyridinemetanol, and 0.34 ml (1.7 mmol) of diisopropylazadicarboxylate were successively added. The mixture was stirred for 5 hours.

After the completion of the reaction, the solvent was then distilled away from the reaction mixture, and the residue was extracted with ethyl acetate three times.

All the ethyl acetate extract layers were mixed and washed with a saturated aqueous solution of sodium chloride and dried over anhydrous magnesium sulfate. The solvent was distilled away from the mixture.

The residue was chromatographed on silica gel, whereby 2-methyl-2-phenoxy-9-(3-pyridylmethoxy)-naphthol [2,3-e]-1,3-dioxan-4-one was obtained in a yield of 558 mg (87%).

IR(cm$^{-1}$, KBr) : 1758

NMR (δ, CDCl$_3$) : 1.94 (3H, s), 5.27 (2H, s), 7.02(1H, d, J=7 Hz), 7.10–7.18(3H, m), 7.25–7.35(2H, m), 7.36–7.44 (2H, m), 7.87(1H, ddd, J=7 Hz, 2 Hz, 2 Hz), 7.91 (1H, s), 8.63(1H, s), 8,66(1H, dd, j=5 Hz, 2 Hz), 8.81(1H, d, J=2 Hz)

Mass (EI) : m/z 431(M'), 371,320,277,185

Melting Point: 171° C.–172° C.

EXAMPLE 4

[Preparation of N-[2-[4-(benzhydryloxy)piperidino]ethyl]-3-hydroxy-5-(3-pyridylmethoxy)-2-naphthamide]

and dried over anhydrous magnesium sulfate. The solvent was distilled away from the reaction mixture.

The residue was chromatographed on silica gel, whereby N-[2-[4-(benzhydryloxy)piperidino]ethyl]-3-hydroxy-5-(3-pyridylmethoxy)-2-naphthamide was obtained in a yield of 344 mg (91%).

IR(cm$^{-1}$, KBr): 1660

NMR (δ, CDCl$_3$): 1.70–1.85(2H, m), 1.92–2.03 (2H, m), 2.18–2.30(2H, m), 2.63 (2H, t, J=6 Hz), 2.81–2.92 (2H, m), 3.37–3.57(3H, m), 5.23 (2H, s), 5.54(1H, s), 6.88(1H, d, J=7 Hz), 7.19–7.42 (14H, m), 7.71(1H, s), 7.89(1H, d, J=7 Hz), 7.94(1H, s), 8,62(1H, dd, J=6 Hz, 2 Hz), 8.74(1H, d, J=2 Hz)

EXAMPLE 5

[Preparation of methyl 3-hydroxy-5-(3-pyridylmethoxy)-2-naphthoate]

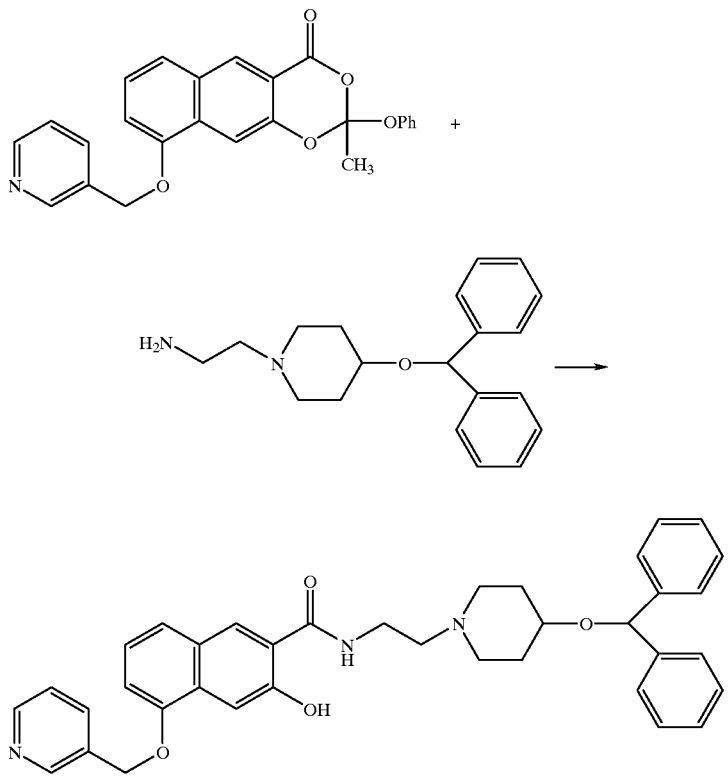

420 mg (1.35 mmol) of 1-(2-aminoethyl)-4-benzhydryloxypiperidine was added to a solution of 226 mg (0.64 mmol) of 2-methyl-2-phenoxy-9-(3-pyridylmethoxy)-naphthol [2,3-e]-1,3-dioxan-4-one prepared in Example 3 in 10 ml of acetonitrile at room temperature. The mixture was refluxed for 7 hours.

After the completion of the reaction, the solvent was then distilled away from the reaction mixture, and the residue was extracted with ethyl acetate three times.

All the ethyl acetate extract layers were mixed and washed with a saturated aqueous solution of sodium chloride

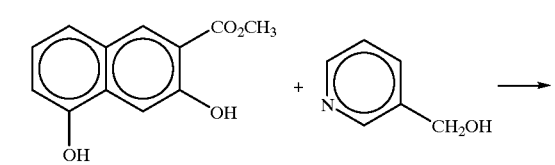

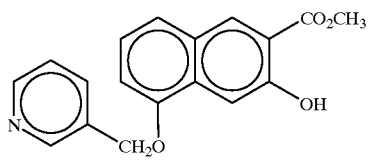

20 g (91.7 mmol) of methyl 3,5-dihydroxy-2-naphthoate, 8.9 ml (91.7 mmol) of 3-pyridinemethanol and 23.2 g (110.0 mmol) of triphenylphosphine were dissolved in 800 ml of anhydrous tetrahydrofuran.

To this solution, 18.2 (91.7 mmol) of diisopropylazadicarboxylate was added dropwise, and the reaction mixture was stirred for 2 hours.

After the completion of the reaction, the solvent was then distilled away from the reaction mixture, and the residue was extracted with ethyl acetate.

The ethyl acetate extract layer was washed with a saturated aqueous solution of sodium chloride and dried over anhydrous magnesium sulfate. The solvent was distilled away from the reaction mixture.

The residue was chromatographed on silica gel, whereby methyl 3-hydroxy-5-(3-pyridylmethoxy)-2-naphthoate was obtained in a yield of 22.7 g (80%).

NMR (δ, CDCl$_3$) ; 4.02 (3H, s), 5.22 (2H, s), 6.90(1H, d, J=8 Hz), 7.22(1H, dd. J=8 Hz), 7.37 (1H, dd, J=8 Hz, J=5 Hz), 7,43(1H, d, J=8 Hz), 7.74(1H, s), 7.88(1H, d, J=8 Hz), 8.45(1H, s), 8.62(1H, d, J=5 Hz), 8.75(1H, s), 10.44(1H, s)

IR(cm$^{-1}$, KBr) ; ν1680 (C=O)

Melting Point; 99.3–100.5° C.

TLC Rf; 0.10 (CHCl$_3$)

EXAMPLE 6

[Preparation of N-[2-[4-(benzhydryloxy)piperidino]ethyl]-3-hydroxy-5-(3-pyridylmethoxy)-2-naphthamide]

40 mg of 60% sodium hydride was added to a solution of 2.98 g (10 mmol) of methyl 3-hydroxy-5-(3-pyridylmethoxy)-2-naphthoate and 3.26 (10.5 mmol) of 1-(2-aminoethyl)- 4-benzhydryloxypiperidine in toluene.

The mixture was refluxed for 5 hours. The reaction solution was cooled to room temperature, washed with 50 ml of water, and dried over anhydrous magnesium sulfate. The solvent was distilled away from the reaction solution.

The residue was chromatographed on silica gel, whereby N-[2-[4-(benzhydryloxy)piperidino]ethyl]-3-hydroxy-5-(3-pyridylmethoxy)-2-naphthamide was obtained in a yield of 5.22 g (91%).

NMR (δ, CDCl$_3$) ; 1.70–1.85 (2H, m), 1.95–2.08 (2H, m), 2.23–2.40 (2H, m), 2.65(2H, t, J=6 Hz), 2.80–2.92 (2H, m), 3.49–3.62 (3H, m), 5.23 (2H, s), 5.54 (1H, s), 6.88 (1H, d, J=7 Hz), 7.18–7.45 (13H, m), 7.55 (1H, br-s), 7.73(1H, s), 7.88 (1H, d, J=7 Hz), 7.94(1H, s), 8.61 (1H, dd, J=4 Hz, J=2 Hz), 8.74 (1H, d, J=2 Hz)

IR(cm$^{-1}$, KBr) ; ν1660 (C=O)

Melting Point; 136° C.–137° C.

TLC Rf; 0.5 (CH$_2$ Cl$_2$ MeOH=95:5)

EXAMPLE 7

[Preparation of N-[2-[4-benzhydryloxy)piperidino]ethyl]-3-hydroxy-5-(3-pyridylmethoxy)-2-naphthamide]

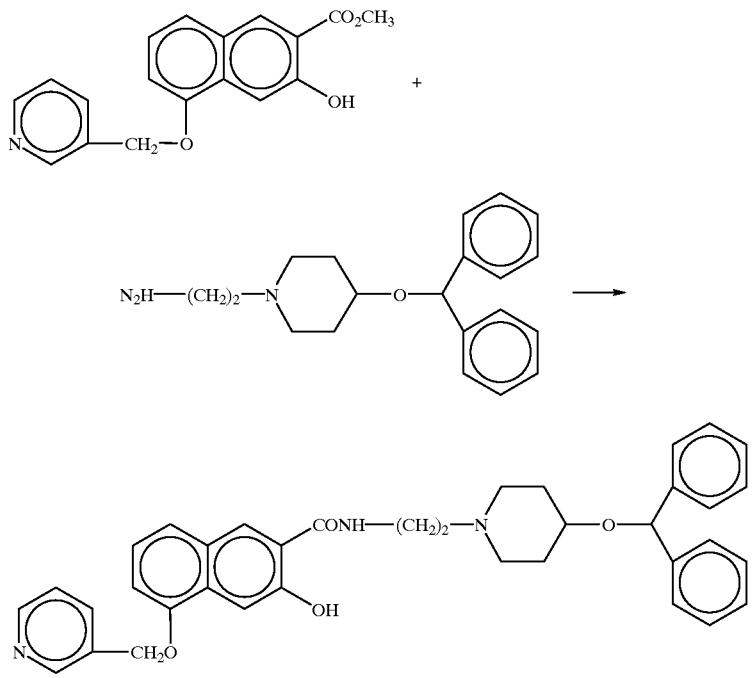

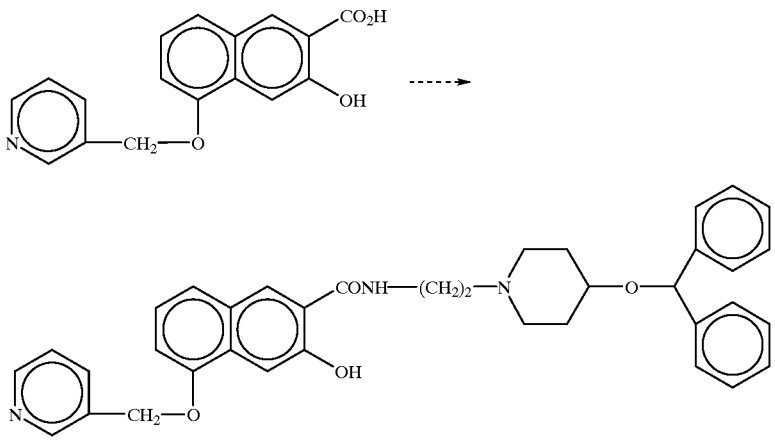

1.18 g (4.0 mmol) of 3-hydroxy-5-(3-pyridylmethoxy)-2-naphthoic acid and 2.24 ml (8.0 mmol) of triethylamine were dissolved in 50 ml of anhydrous methylene chloride.

To this solution, a solution of 0.96 ml (8.0 mmol) of pivaloylchloride in 5 ml of anhydrous methylene chloride was added dropwise at 0° C., and the mixture was stirred for 2 hours.

The solvent was distilled away from the above reaction mixture under reduced pressure. The residue was dissolved in 100 ml of ethyl acetate.

The solution was washed successively with water, an aqueous solution of sodium bicarbonate, and a saturated aqueous solution of sodium chloride, dried over anhydrous sodium sulfate, and filtered.

To the filtrate, 1.12 ml (4.0 mmol) of triethylamine was added. To the mixture was added dropwise at 0° C. a solution of 1.49 g (4.8 mmol) of 1-(2-aminoethyl)-4-benzhydryloxypiperidine in 5 ml of ethyl acetate.

This reaction mixture was stirred for 2 hours, and concentrated under reduced pressure.

The residue was dissolved in 60 ml of methanol. To this solution, an aqueous solution of 1.66 (12.0 mmol) of potassium carbonate in 16 ml of water was added. The mixture was stirred at room temperature for 1 hour.

The solvent was distilled away from the reaction mixture under reduced pressure, and the residue was dissolved in 200 ml of ethyl acetate.

This solution was then washed with water, an aqueous solution of ammonium chloride, and a saturated aqueous solution of sodium chloride, and dried over anhydrous sodium sulfate.

The solvent was distilled away from the mixture under reduced pressure.

The residue was chromatographed on silica gel, whereby N-[2-[4-benzhydryloxy)piperidino]ethyl]-3-hydroxy-5-(3-pyridylmethoxy)-2-naphthamide was obtained in a yield of 1.53 g (65%).

NMR (δCDCl$_3$) ; 1.70–1.85 (2H, m), 1.95–2.08 (2H, m), 2.23–2.40 (2H, m), 2.65(2H, t, J=6 Hz), 2.80–2.92 (2H, m), 3.49–3.62(3H, m), 5.23 (2H, s), 5.54 (1H, s), 6.88 (1H, d, J=7 Hz), 7.18–7.45 (13H, m), 7.55(1H, br-s), 7.73(1H, s), 7.88(1H, d, J=7 Hz), 7.94(1H, s), 8.61(1H, dd, J=4 Hz, J=2 Hz), 8.74(1H, d, J=2 Hz).

IR(cm$^{-1}$, KBr) ; v1660 (C=O)

Melting Point; 136°–137° C.

TLC Rf; 0.5 (CH$_2$Cl$_2$ : MeOH=95:5)

Japanese Patent Applications Nos. 7-160161, 7-160162, and 7-160163, respectively filed on Jun. 5, 1995, are hereby incorporated by reference.

What is claimed is:

1. A compound of formula (VI-a),

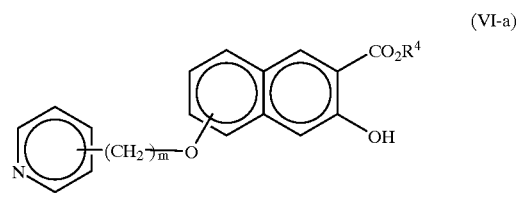

(VI-a)

wherein R$^4$ is an unsubstituted alkyl group having 1 to 6 carbon atoms; and m is an integer of 1 to 6.

2. The compound of formula (VI-a) according to claim 1, wherein R$^4$ is an unsubstituted alkyl group selected from the group consisting of methyl group, ethyl group, propyl group, isopropyl group, n-butyl group, sec-butyl group, t-butyl group, pentyl group and hexyl group.

3. The compound of formula (VI-a) according to claim 1, wherein R$^4$ is an unsubstituted methyl group.

* * * * *